United States Patent [19]

Schindler et al.

[11] Patent Number: 4,624,915
[45] Date of Patent: Nov. 25, 1986

[54] POSITIVE SELECTION SORTING OF CELLS

[75] Inventors: Melvin S. Schindler, Okemos; John F. Holland, Lansing, both of Mich.

[73] Assignee: Board of Trustees of Michigan State University, East Lansing, Mich.

[21] Appl. No.: 513,995

[22] Filed: Jul. 14, 1983

Related U.S. Application Data

[63] Continuation-in-part of Ser. No. 403,154, Jul. 29, 1982.

[51] Int. Cl.$^4$ .......................... C12N 5/00; C12M 1/34; C12Q 1/00
[52] U.S. Cl. ........................................ 435/4; 435/240; 435/291
[58] Field of Search ...................... 356/39, 73; 422/22, 422/52, 68; 436/63, 172; 250/458.1, 461.1, 461.2, 222.2, 239, 304, 361 R, 461, 492.2, 564, 574, 575; 435/4, 6, 29, 30, 39, 173, 241, 245, 261, 291, 297, 310, 800, 808; 209/3.1, 3.3, 44.1, 540, 541, 552, 578, 579, 644, 906, 932, 934

[56] References Cited

U.S. PATENT DOCUMENTS

| | | | |
|---|---|---|---|
| 3,712,746 | 1/1973 | Bergeron | 435/808 |
| 3,941,670 | 3/1976 | Pratt, Jr. | 422/22 |
| 3,984,307 | 10/1976 | Kamentsky et al. | 356/39 |
| 4,045,772 | 8/1977 | Bouton et al. | 356/39 |
| 4,090,128 | 5/1978 | Simpson et al. | 356/39 |
| 4,090,921 | 5/1978 | Sawamura et al. | 435/808 |
| 4,172,227 | 10/1979 | Tyrer et al. | 250/461.2 |
| 4,175,662 | 11/1979 | Zöld | 209/552 |
| 4,204,117 | 5/1980 | Aberle et al. | 250/461.2 |
| 4,209,256 | 6/1980 | Faulkner | 356/73 |
| 4,284,897 | 8/1981 | Sawamura et al. | 250/461.2 |
| 4,354,114 | 10/1982 | Karnaukhov et al. | 250/461.2 |
| 4,395,397 | 7/1983 | Shapiro | 435/289 |
| 4,513,438 | 4/1985 | Graham et al. | 382/6 |

FOREIGN PATENT DOCUMENTS

80/00188 2/1980 PCT Int'l Appl. ................... 422/52
2100425 12/1982 United Kingdom ..................... 435/4

OTHER PUBLICATIONS

Cell Separation: Methods and Selected Applications, Pretlon, II, T. G. et al, ed., Academic Press, New York, pp. 193–198 (1982).
The Coulter ® EPICS ® V System, brochure, Coulter Electronics, Inc., Rev. Apr. 1982.
Higgins et al, 1980, "Selective Cell Destruction and Precise Neurite Transection . . . " J. Neuroscience Methods, v3, pp. 83–99.
Bessis, 1970, "Selective Destruction of Cell Organelles by Laser Beam" Adv. in Biol. and Medical Physics, v13, pp. 209–218.
Koppel, 1979, "Fluorescence Redistribution after Photobleaching" Biophys. J. v28, pp. 281–292.
Koppel, D. E. et al, Biophysics Journal 28:281–291 (1979).
Higgins, et al., J. Neurosc. Meth., 3, 1, 1980.
Lepock, et al., Biochem. Biophys. Res. Comm. 91, 3, 1979.
Berns, in Jour. Cell Biol. 75, 3, 1975.

Primary Examiner—Thomas G. Wiseman
Assistant Examiner—Joanne M. Giesser
Attorney, Agent, or Firm—Miller, Morriss & Pappas

[57] ABSTRACT

A method and apparatus for position selection of viable cells based upon differing chemical or physical properties or dynamic processes using a focussed radiant energy beam, such as a laser beam (11) to kill unwanted cells or to isolate wanted cells is described. The apparatus includes microscope means (14) and cell detection means (27) for identifying the cells to be killed or saved and attenuator means (12) for modifying the beam to prevent destruction of cells to be saved.

8 Claims, 9 Drawing Figures

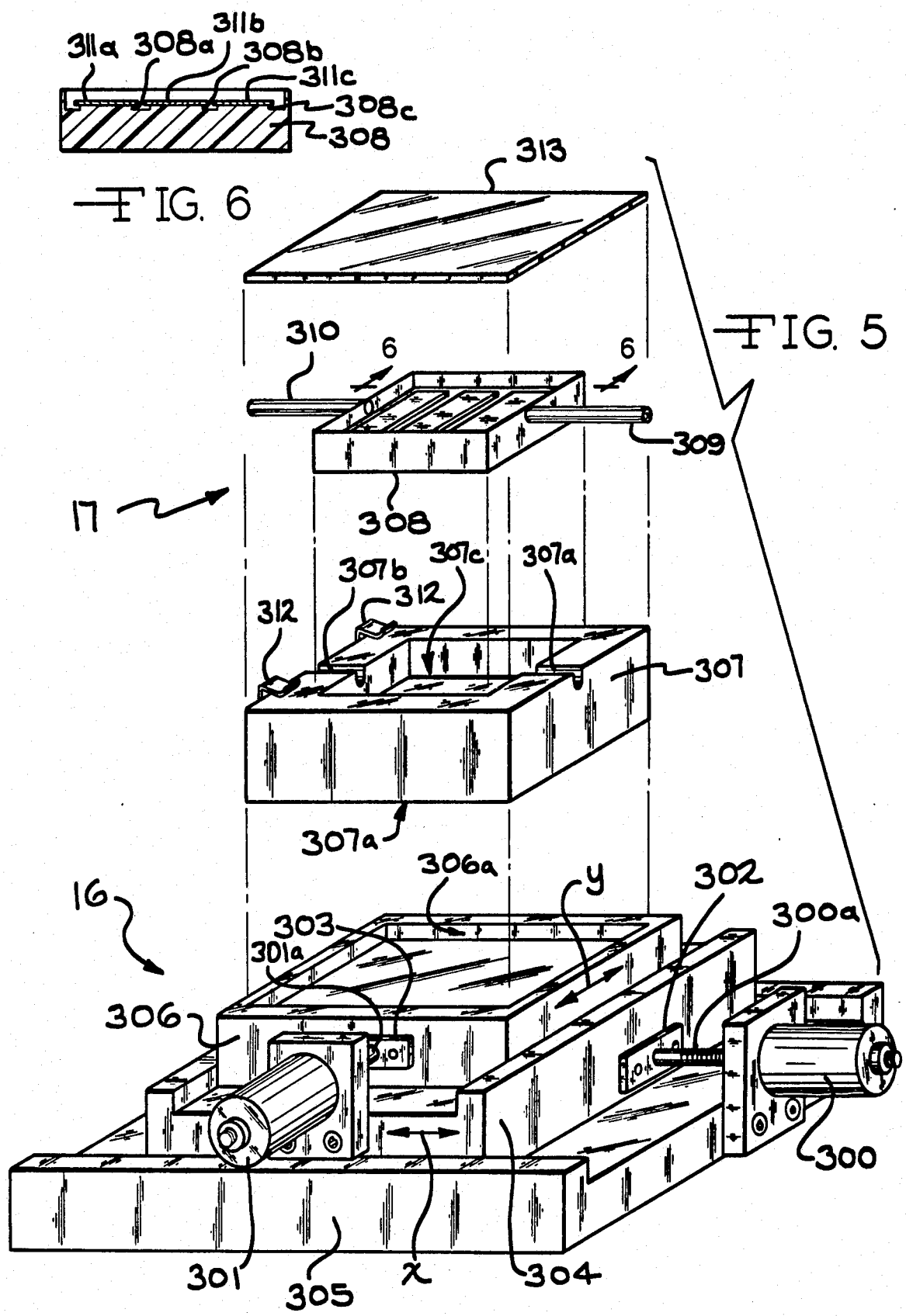

POSITIVE SELECTION SORTING OF CELLS

CROSS REFERENCE TO RELATED APPLICATION

This application is a continuation-in-part of application Ser. No. 403,154 filed July 29, 1982 which is pending.

BACKGROUND OF THE INVENTION

The present invention relates to an apparatus and a method for sorting a population of living cells based upon differing chemical or physical properties or dynamic process capabilities. The method uses a radiant energy beam (11, 15) for destroying unwanted cells and/or circumscribing around wanted cells in the population.

Prior Art

In general in the prior art, a central feature of the chemical analysis of complex mixtures is the isolating and purification of specific compounds. These purified homogeneous components are subsequently characterized with regard to their physical properties. In the past, for cell biochemistry this implied the isolation from the cell of an enzyme or receptor protein by gel chromatography with the attendant destruction of the cell.

With the advent of newer culture techniques and defined media, it has become possible to grow all types of cell lines in culture. This has provided for the possibility of growing sufficient quantities of cells to do biochemical analysis on cell and membrane components. A major problem in this approach, however, is the large variability of cell surface structure leading to altered function within a relatively specific family or population of cells. For example, T-cells of the immune system have sub-populations of cells with altered properties and function. These observations have stimulated researchers to develop methodologies and instrumentation for the purpose of separating the cells into distinct sub-populations on the basis of a defined characterization in a direct analogy to the conceptual approaches of protein separation and purification mentioned above. Mixed polymer systems have been employed to separate cells based on surface properties, cell electrophoresis has been used to separate cells by surface charge, and solid phase lectins and antibodies have been exploited to differentiate between altered structural determinants in membrane proteins for cell separation.

Recently, fluorescence measuring cell sorters have become commercially available. The great advantage of the method and apparatus of these devices is that they efficiently separate a large population of cells based on differences in bound fluorescent probes (usually an antibody or lectin containing a covalently attached fluorophore). Specific selection of parameters are established in these prior art instruments. Cells are sorted into separate tubes based on fluorescent or other light interactive behavioral differences. Sorted cells can be run through the system a number of times to provide further enrichment. In this manner, approximately $1 \times 10^7$ cells, an amount sufficient for characterization, could be sorted in 1 to 2 hours.

The fluorescence activated cell sorter (FACS Systems, Becton Dickinson of Sunnyvale, Calif. U.S.A. and Coulter Electronic, Inc. of Hialeah, Fla.) are computer centered, single laser units capable of analyzing and separating individual cells on the basis of fluorescence, size and viability. The electronic and recording measurements can be made with or without sorting. Sorting is accomplished by electrostatic induction on individual cells in a flow system. The laser is used as a light source for the fluorescence. The cytofluorograph system (Ortho Diagnostic Systems, Inc. of Westwood, Mass.) utilizes two laser beams in the same manner and separates again by electrostatic induction based upon measurements of size, fluorescence and/or refraction indices.

Although this prior art methodology and apparatus represent a major technological breakthrough with regard to obtaining a homogeneous population of cells based upon chemical properties, its usefulness is limited in the following ways:

(1) since all are flow through systems, they are susceptible to the pump and clogging problems observed in any fluid system;

(2) maintaining sterile conditions through long lengths of plastic tubing through which the cells must pass is very difficult;

(3) the buffeting and collisions encountered by cells flowing through the sorter can have deleterious effects on cell membranes, causing unknown cellular responses, in some cases cell death;

(4) cell differentiation in most instances is determined only by structural markers attached to the cells which does not take advantage of the ability to isolate and separate cells based on altered membrane properties such as the rotational and translational diffusion differences of cell surface components. These parameters have been shown to be important in cell stimulatory events, e.g.-hormones and growth factors;

(5) a major drawback in flow cytometry sorters is the necessity to use cells in suspension for separation. This precludes the use of this technique for the sorting of cells growing in culture mounted on a plate or surface. The properties of cells can change dramatically with shape; it is therefore essential to sort them as close to their normal shape as possible. In addition, there has been a strong correlation made between cell shape and ultimate function, both of which are affected by the surface on which the cells grow. Clearly, it would be desirable to separate the cells while growing on specific surfaces. This is not possible with the commercial units.

The prior art in Koppel, D. E. et al Biophysics Journal 28:281-291 (1979) has described the use of lasers for irradiating cells mounted on a plate with light energy sufficient to photobleach a spot on a surface of the cell and then to follow the progress of the migration of fluorescently labeled molecules back into the bleached area.

In the Koppel et al apparatus, occasionally the cells can be accidentally killed by the laser beam; however, the apparatus is adapted only for practice of the bleaching method. No provision is made for providing a supply of nutrient medium to the cells and thus there is no means for removing the enzymes and other cell components left in the event the cells are killed. Such components seriously affect the remaining living cells. The Koppel apparatus has never been used in a method for cell sorting.

Other prior art practices include cell or cellular component destruction by laser energy, such as by Higgins, et al., J. Neurosc. Meth., 3, 1, 1980; Bessis in Advances in Biological and Medical Physics, Academic Press, New York; 1970; Mosley, et al., in Proc. Natl. Acad.

Sci. 78, 9, 1981; Lepock, et al., Biochem. Biophys. Res. Comm. 91, 3, 1979; and Berns in Jour. Cell Biol. 75, 3, 1975.

All of these utilize the destructive power of ultraviolet or coherent radiation for the purpose of destroying selected targets, not for the purpose of cell progeny selection in a life sustaining environment. The application of this prior art involves ablation studies, cell suicide studies (negative selection), Organelle micro-surgery, therapeutic cell destruction and other areas not relating to cell sorting.

Objects

It is therefore an object of the present invention to provide a positive selection cell sorting apparatus and method which uses electromagnetic radiation beam (11) generating means (10) with attenuator means (12) for the beam for cell destruction of unwanted cells and/or for circumscribing around wanted cells for the purpose of cell sorting under the most ideal cell conditions.

Further it is an object of the present invention to provide computer (101) control of the destruction of cells by the beam (11) generating means (10). It is further an object to provide an apparatus having the ability to sort cells provided on an environmentally controlled plate (17).

It is further an object to provide an apparatus which utilizes cellular properties as well as label recognition as the basis of cell selection.

It is further an object of the present invention to provide an apparatus which has the ability to engage in long term selection processes which can utilize dynamic cellular behavior processes as the basis for cell differentiation.

It is also an object to provide an apparatus which has the ability to use more than one cell parameter as a basis for selection of cells. Such as for example, selection on the basis of a physical characteristic when immature and selection on the basis of a membrane characteristic when mature and including the possibility for multi-dimensional schemes in sequence for more refined selection at any cell stage.

It is an object to provide more effective and efficient sorting processes performed on cells in their natural configuration without perturbation.

It is an object to provide an apparatus which is useful with cell types that are not amenable to the transport selection processes of the prior art.

Finally it is an object to provide an apparatus which has the ability to monitor without destruction variations in individual cells during incubation where subsequent save or destroy options determine cellular fate.

These and other objects will become increasingly apparent by reference to the following description and the drawings.

IN THE DRAWINGS

FIG. 5 is an isometric exploded view of the plate (17) shown in FIG. 2 showing an x-y moveable stage (16) for the plate (17).

FIG. 6 is a front cross-sectional view of the plate (17) shown in FIG. 5.

GENERAL DESCRIPTION

Figure 1:
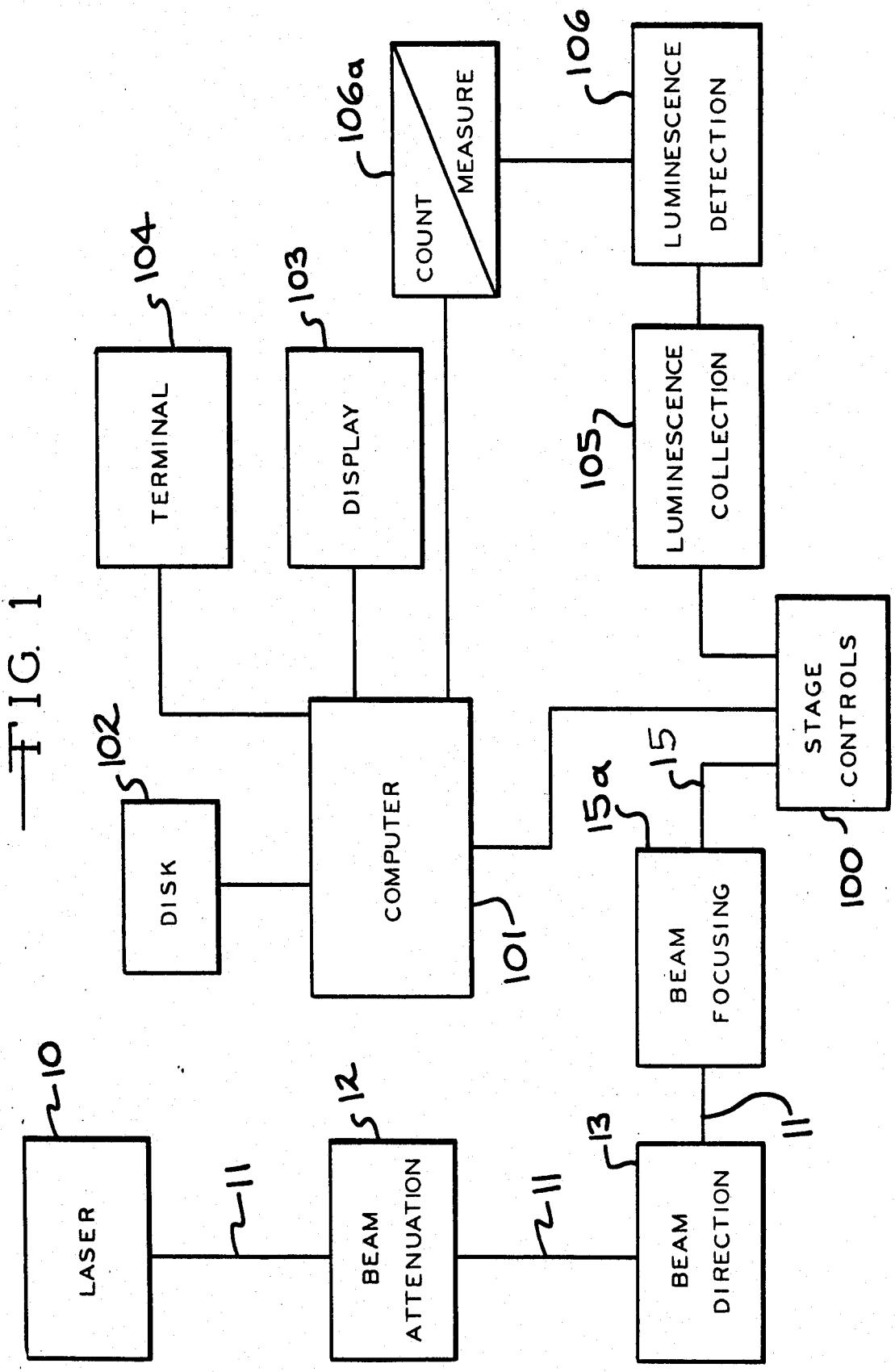
FIG. 1 is a block diagram of the preferred positive selection cell sorting apparatus used in the method of the present invention.

The present invention relates to an apparatus for sorting a heterogeneous population of living cells into a segregated population based upon chemical or physical properties or dynamic processes by selection for wanted cells which comprises:

(a) microscope means (14) with an objective (15a) for scanning a heterogeneous population of cells fixed on a plate (17, 311) or on a film (312) removably mounted on the plate positioned adjacent the objective on a coordinate scanning or an individual cell-by-cell scanning basis, wherein the plate or film on the plate is adapted to contain a flowing liquid growth medium for the cells;

(b) detection means (27, 106) for distinguishing an individual cell based upon a particular chemical or physical property or dynamic processes as determined by the detection means through the objective;

(c) focussed radiant energy beam (11, 15) generating means (10, 11, 12, 13, 15a) associated with the microscope means such that the beam can be focussed in a path through the objective at the plate and at or around an individual cell or series of cells on the plate; and (d) controlled interruption means (12) for selectively attenuating the beam, wherein the beam can irradiate or circumscribe individual cells on the plate or on the film on the plate when the interruption means is removed from the path.

The present invention further relates to a preferred apparatus for sorting a heterogeneous population of living cells into a segregated population based upon physical or chemical properties or dynamic processes which comprises:

(a) microscope means (14) with an objective for viewing a heterogeneous population of cells, which are fixed on a plate (17, 311) or on a film (312) removably mounted on the plate, with the plate positioned adjacent the objective on a coordinate scanning or an individual cell-by-cell scanning basis, wherein the plate or film on the plate is adapted to contain a flowing liquid growth medium for the cells;

(b) drive means (100) for moving the plate beneath the objective or for moving the objective or beam across the plate in an x-y coordinate plane or for both such that the objective scans and views each of the cells in the heterogeneous population;

(c) detection means (27, 106) for distinguishing an individual cell based upon a particular chemical or physical property or dynamic processes determined by the detection means through the objective;

(d) focussed radiant energy beam (11, 15) generating means (10, 11, 13, 15a) with lenses (22) and mirrors (13a, 13b, 13c, 13d, 13e) positioned for directing the beam in a path through the objective and at or around an individual cell or a series of cells viewed by the objective;

(e) attenuator means (32, 33, 34, 35, 36) moveable into the beam for selectively attenuating the beam;

(f) controlled means (32, 33, 34, 35, 36) for selectively providing the attenuator means into the path of the beam, wherein the detection means distinguishes cells to be saved when the attenuator means is positioned between the objective and the beam by the controlled means and wherein the attenuator means is removed from the path of the beam by the controlled means in order to use the beam to select for unwanted or wanted cells by killing unwanted cells or by fusing the film onto the plate supporting the cells around the wanted cells with the beam or by cutting around a film removably adhered to the plate and then removing the film with the unwanted cells fixed to the film.

The present invention also relates to a method for selecting for wanted metabolizing living cells which comprises:

(a) providing the cells fixed on a plate (17, 311) or a film (312) mounted on the plate beneath a microscope means (14) with an objective (15a) wherein the objective views the cells on an individual cell-by-cell or series of cells basis and wherein the plate contains a flowing liquid growth medium for the cells; and (b) selectively attenuating (28, 29, 30, 31) the beam (11) such that cells to be saved are not irradiated with the unattenuated beam and such that the cells to be saved are selected based upon a light response to the attenuated beam; and (c) selectively irradiating at or around the individual cells or series of cells with a focussed radiant energy beam (11, 15) through the objective (15a) of the microscope means with sufficient energy to kill unwanted cells on the plate or to circumscribe wanted cells on the film so that the wanted cells are separated with a portion of the film and remain on the plate and the unwanted cells are removed.

Finally the present invention relates to a preferred method for sorting a heterogeneous population of cells into a segregated population based upon physical or chemical properties or process capabilities by selectively killing unwanted cells or by retaining wanted cells which comprises:

(a) providing a cell sorting apparatus including a microscope (14) with an objective (15a) for viewing a heterogeneous population of cells fixed on a plate (17, 311) or a film (312) mounted on the plate positioned adjacent the objective on a coordinate scanning or an individual cell-by-cell scanning basis wherein the plate or the film on the plate contains a flowing liquid growth medium for the cells;

drive means (100) for moving the plate and container beneath the objective or for moving the objective or beam across the plate in an x-y coordinate plane or for both such that the objective scans and views each of the cells in the heterogeneous population;

detection means (27, 106) for distinguishing an individual cell based upon a particular chemical or physical property or dynamic process determined by the detection means through the objective;

focussed radiant energy beam (11, 15) generating means (10, 11, 13, 15a) with lenses (22) and mirrors (13a, 13b, 13c, 13d) positioned for directing the beam in a path through the objective at or around an individual cell or a series of cells viewed by the objective;

attenuator means (28, 29, 30, 31) moveable into the path of the coherent light beam for selectively attenuating the beam;

controlled means (32, 33, 34, 35) for selectively providing the attenuator means into the path of the beam, wherein the detection means distinguishes cells to be saved when the attenuation means is positioned between the objective and the beam and wherein the attenuator means is removed from the path of the beam by the controlled means in order to use the beam to select for unwanted or wanted cells by killing unwanted cells or to circumscribe the wanted cells by fusing the film onto the plate supporting the cells around the wanted cells with the beam or by cutting around a film removably adhered to the plate with the beam and then removing the film with the unwanted cells fixed to the film;

(b) sorting the cells by selectively allowing the beam to kill unwanted cells or to circumscribe the wanted cells with the beam by removal of the attenuator means from the beam.

SPECIFIC DESCRIPTION

Optical System

Figure 2:
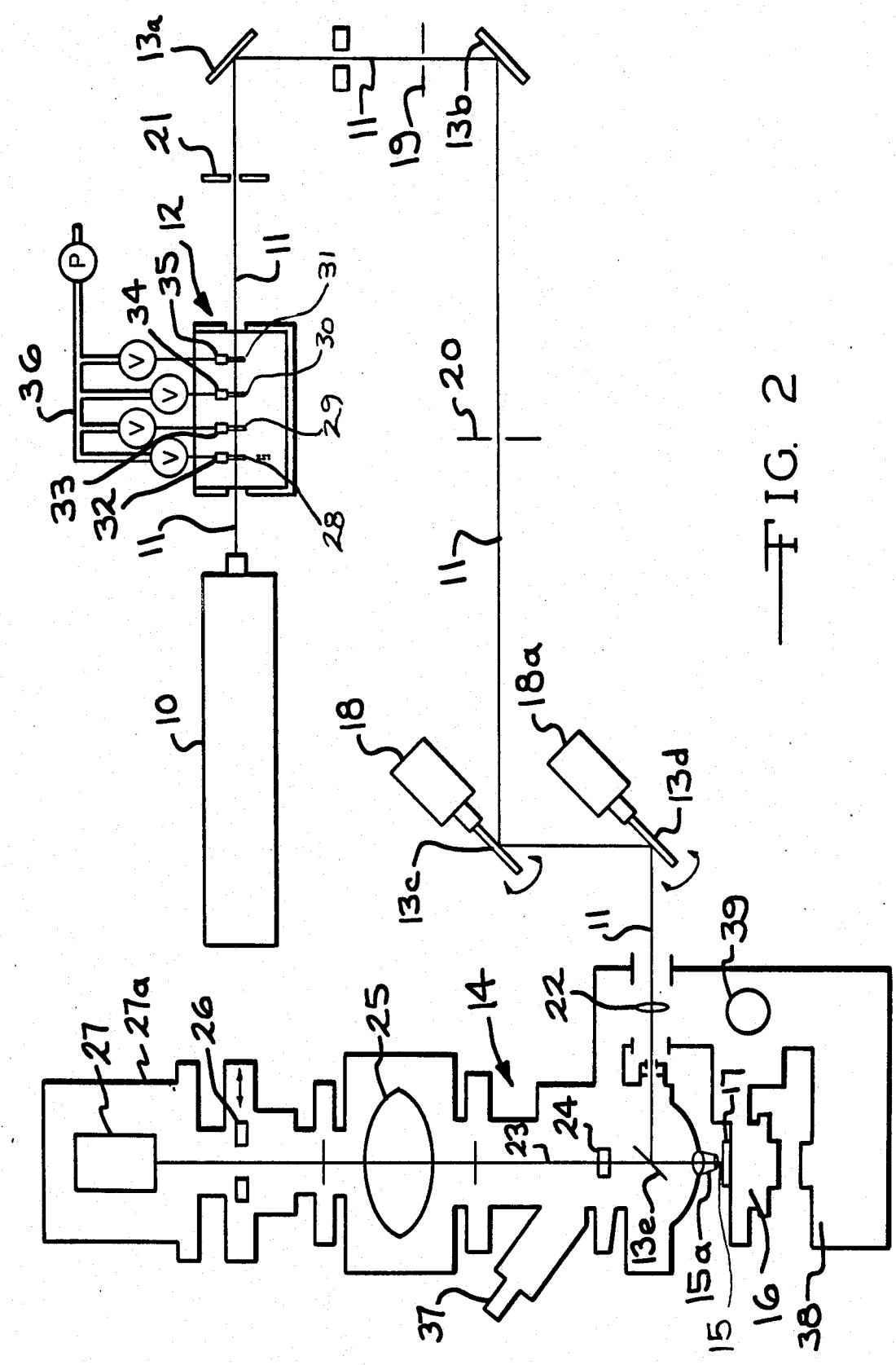
FIG. 2 is a schematic view of the laser (10), beam attenuator (12) and microscope means (14) in the preferred apparatus of the present invention.

Referring to FIGS. 1 and 2 a focussed radiant energy beam generating means, such as a laser 10, generates a beam 11. The laser 10 is preferably of the argon type and capable of generating light in wavelengths between about 300 and 560 nanometers. The beam 11 is filtered by beam attenuation means 12 provided in the path of the beam 11. Beam deflection means 13, such as mirrors, 13a, 13b, 13c, 13d and 13e shown in FIG. 2, are used to provide the beam 11 inside a microscope 14. A focussed beam 15 is provided by an objective 15a. The focussed beam 15 measures about 1 micron in diameter compared to cells of a much greater dimension, for example 40 microns in diameter with nucleus of about 10 microns in diameter.

A microscope stage 16 supports plate 17 for supporting the immobilized cells (not shown). The stage 16 is moveable in an x and y plane perpendicular to the focussed beam 15 as discussed in connection with FIG. 5. The mirrors 13c and 13d are moveable by motors 18 and 18a so as to provide scanning of the plate 17 in the x and the y plane by the focussed beam 15. If the stage 16 moves as described hereinafter, then the motors 18 and 18a are unnecessary. Diaphragms 19 and 20 can be used to regulate the beam as can shutter 21. Lens 22 contributes to movement of the beam 15 in the x or y coordinate without distortion when mirrors 13c and 13d are moved.

Mirror 13e is a dichromatic mirror such that emitted light 23 from the plate 17 passes through the mirror 13e. A barrier filter 24 allows only selected luminescence to pass. A mirror or grating element 25 is positioned in the path of the reflected light 23. A shutter 26 allows instantaneous passage of light to a photo multiplier tube 27.

The basic elements of the laser microscope apparatus (without the attenuator means 12 or the unique moveable stage 16 as discussed hereinafter) are described in detail in the Koppel article discussed previously. The laser is available from Lexel, Inc., Sunnyvale, Calif.; the microscope is available from Leitz, Inc., Rockleigh, N.J. and the moveable mirrors 13c and 13d are available from General Scanning, Inc., Waterstown, Mass.

The beam attenuation means 12 includes filters 28, 29, 30 and 31 which are moveable into and out of the beam 11 path by means of pneumatic actuators 32, 33, 34 and 35. Filter 28 is moved to position 28a out of the beam 11 path by the actuator 32 as shown by the dotted lines. The remaining filters 29 to 31 are moved in the same manner. Valves V control the movement of the actuators 32 to 35. Pneumatic lines 36 provide air under pressure to valves V.

The microscope includes a conventional binocular viewing means 37, support 38 and a manual adjustment knob 39.

Electronic Configuration

Figure 3:
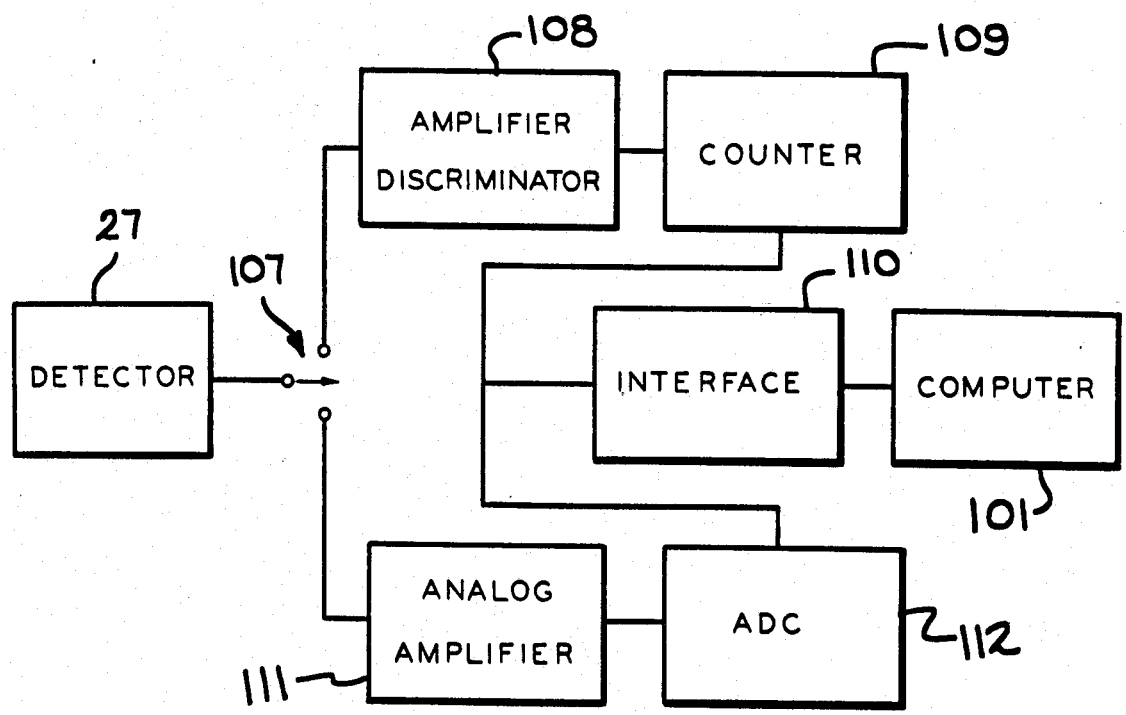
FIG. 3 is a block diagram showing the interface between the detection means (27, 106) and the computer (101) in the preferred apparatus.

Referring to FIGS. 1 and 3, the electronic elements of the present invention are illustrated. The stage 16 is provided with electrically actuatable controls 100, as described more fully hereinafter, to provide movement of the stage 16 in the x-y plane perpendicular to the beam 11. Alternatively the motors 18 and 18a for mirrors 13c and 13d can be electrically moveable. The stage 16 movement is controlled by a computer 101 driven by a program stored on a disc(s) 102. The computer 101 can include video display 103 and recorder (not shown) connected to terminal 104. The microscope 14 functions as a fluorescence collection unit 105 from the stage 16. The photomultiplier tube 27 functions for fluorescence detection 106 and includes means 106a for counting and/or measuring the fluorescence which is recorded by the computer 101. Thus the computer 100 controls stage 16 movement and records the presence or absence of fluorescence on the plate 17. For slower operation a system without the computer 100 could be used; however with much less precision and the speed would be prohibitively slow. The lens 15a provides beam 11 focussing, the mirrors 13a to 13e provide beam direction and the beam attenuator 12 provides beam attenuation as previously discussed.

In FIG. 3, the detector or photomultiplier tube 27 is coupled to the computer 101 by means of switch 107 to either: (a) an amplifier discriminator circuit 108 manufactured by Precision Products, Inc., Groton, Conn. and counter 109 through interface 110 to the computer 101; or (b) to a rate measuring circuit using the analog amplifier 111 and a 12 bit analog to digital converter 112. The digital output of this unit is fed to the computer 101 through the interface 110. All of this is state of the art.

Cell Environmental Control

Figure 4:
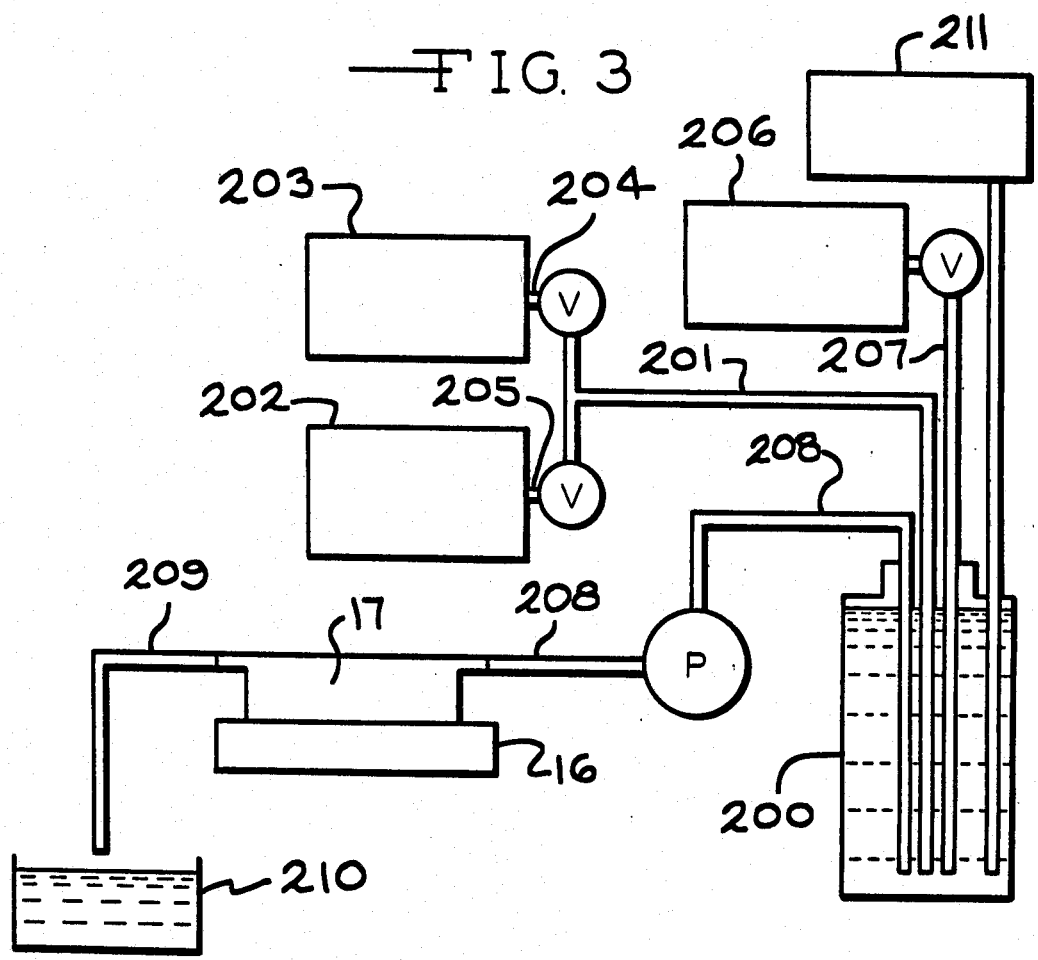
FIG. 4 is a schematic diagram showing preferred means for supplying a continuous flow of nutrient medium to cells on a plate (17) adapted to contain the medium.

FIGS. 4, 5 and 6 show the plate 17 adapted for cell environmental control on stage 16. Container 200 is fed through line 201 with a mixture of cell growth media from containers 202 and 203 controlled by valves V in lines 204 and 205. Container 206 feeds necessary gases to container 200 through valve V in line 207. Pump P supplies the mixed media in container 200 and gases via line 208 to plate 17 as shown more fully in FIGS. 5 and 6. Line 209 releases spent media to a drain or waste container 210. Monitoring of media properties is accomplished by transducers sensitive to temperature, carbon dioxide, oxygen and hydrogen ion activity. These transducers are connected to unit 211.

The stage 16 includes motor 300 for movement in the x direction and by motor 301 for movement in the y direction. The movement is accomplished by screw shafts 300a and 301a. Attached by plates 302 and 303 to a first moveable holder 304 which slides in the x direction on base 305 and to a second moveable holder 306 which slides in the y direction on first holder 304. Such a stage is available from Ealing located in South Natick, Mass.

The second holder 306 is provided with a recess 306a adapted to receive the base 307a of a support 307. The support 307 has spaced apart recesses 307a and 307b and 307c adapted to receive a container 308 with inlet conduit 309 and outlet conduit 310 to be connected to lines 208 and 209 as shown in FIG. 4. The container 308 includes integral pedestals 308a, 308b and 308c which support glass slides 311a, 311b and 311c which support the growing cells. The support 307 includes clips 312 for holding glass cover 313 in position on support 307 to completely cover the plate 308 when the cells are not being viewed by the objective 15a. During viewing of the cells on the slides 311a to 311c by the objective, the cover 313 is removed; however, the media is still allowed to flow across the container 308.

Figure 6A:
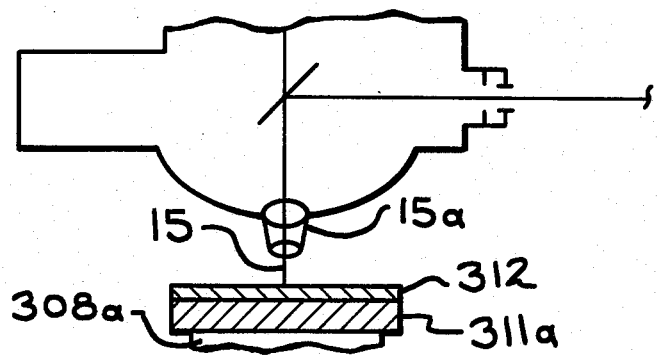
FIGS. 6a, 6b and 6c show one slide (311a) with a film (312) mounted on it such that wanted cells can be circumscribed by the beam (15) and unwanted cells removed with the film (312) except for discs (313) with the wanted cells.
Figure 6B:
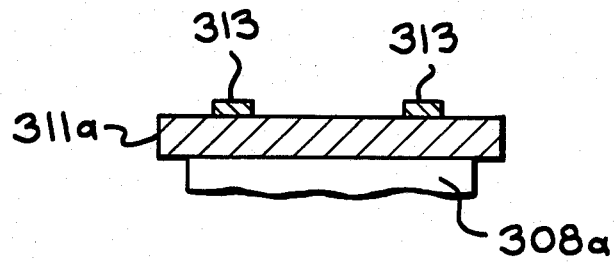
Figure 6C:
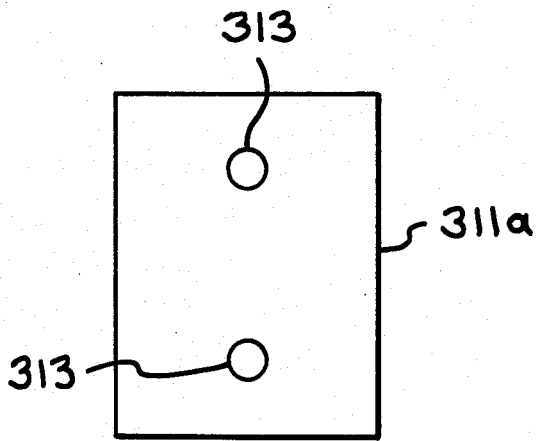

As shown in FIGS. 6a to 6c, a variation of the method of the present invention utilizes a thin film 312 mounted on the slide 311a which supports the cells so that the beam 15 cuts or fuses the film 312 to the slide 311a around the cells for removal of unwanted cells with the film 312. One slide 311a with the thin film 312 as shown in FIG. 3a. The film 312 is generally between about 5 and 200 microns thick is in contact with the slide 311a and the cells grow on the opposite side of the film 312. The film is preferably composed of a thermoplastic material such as polyvinyl chloride. The film 312 can also be removably bonded to the slide 311a with an adhesive so that the beam 15 can cut around the wanted cells and the unwanted cells are removed with the film 312 from the slide 311a. Alternatively the beam 15a can fuse portions of the film 312 to the slide 311a by beam 15 welding. In either case the unwanted cells and film 312 can be stripped from the plate to leave behind discs 313 supporting the wanted cells from film 312 fused onto the slide 311a.

The improved method is valuable in sorting for a few wanted cells in a large number of cells, since it produces little cell debris which can affect the wanted cells. Where there are fewer unwanted cells in the cell population, the unwanted cell killing method is preferred.

Light absorbing materials can be provided on the slide 311a alone or beneath the film 312. This facilitates cell killing or cutting or fusing of the film 312 using the beam 15.

It will be appreciated that the method involving circumscribing wanted cells by cutting or fusing with the beam 15 can be combined with the method involving killing of the unwanted cells. There is no particular advantage in using the combination for one sorting procedure because of the concern for cell debris which affects wanted cells in the culture medium.

Operation

The present invention uses quantitative techniques for the characterization of diffusion in biological membranes which has made it possible to employ laser technology to develop a scanning system capable of selecting a specific sub-population of cells based on a variety of structural and/or physical parameters. The cells do not move because they are supported on slides 311a to 311c or film 312 and can be maintained in a state that is maximally advantageous to the maintenance of cell viability. The central idea of the approach is that cells with the desired property are spared from a pulse of high intensity laser beam 15a capable of destroying them or are circumscribed when they are on the film 312. In this manner, a high level of cell enrichment for the defined characteristic is obtained. A significant feature of this system is that cells cultured on slides 311 or film 312 may be used for enrichment. This advantage greatly increases the ultimate biological relevance of any information obtained by chemical analysis of the resulting sorted cells.

The intensity of the beam 11 is controlled by one or more neutral density filters 28 to 31 inserted or removed from the beam 11 path by air-driven solenoids 32 to 35 that are computer 101 controlled preferably in sixteen (16) discrete levels of attenuation. Alternate devices to effect beam attenuation can be acousto-optical and/or electro-optical. A series of diaphragms and mirrors 13a to 13e then guide the beam into the back of the microscope 14 capable of epi-fluorescence illumination. The microscope objective 15a adjusts the final focus of the laser beam 15 into the plane of the cells. The dichroic mirror 13e reflects the laser beam 11 down through the microscope 14 objective while allowing sample luminescence to be transmitted up to the photomultiplier tube 27 located in a thermoelectrically cooled housing 27a. The electronic shutter 26 placed in front of the tube 27 acts to protect the tube 27 from high levels of irradiation. The signal from the tube 27 is fed to a computer 101 for processing and output.

The essential feature of positive cell selection is the maintenance of optimal growth conditions during the sorting cycle. The microflow container 308 provides a controlled environment for cells which can be further controlled by the computer 101 (not shown). This container 308 is preferably metallic and provides a thermal reservoir for temperature control, flow selection and regulating valves for media flow and gas mixing by the system shown in FIG. 4. This container 308 also provides for time dependent alterations, e.g. discrete growth substance addition, timed light exposure, etc. Sterility of growing cultures is maintained by the flow properties of the container 308. For short working distance the objective 15a is sterilized before use and is positioned in the growth medium. For long working distance objectives, immersion is not necessary. Cells are grown in container 308 preferably with about one hundred forty-four mm² area continuously bathed by the flowing media.

For the purpose of cell sorting, three operational modes can be utilized. Cell sorting on the basis of a fluorescence marker recognition; cell sorting on the basis of a measured physical property; and cell sorting on the basis of a measured dynamic process (time dependent) characteristic.

The selection occurs as follows. The cells are grown on slides 311a to 311c which can have the film 312 on it. The edges of these slides 311a to 311c (or film 312) are coated with a strong fluorophore (not shown). A low intensity scout beam 15 traverses an (x) coordinate of the field. On its return on the same coordinate, the high intensity beam 15 is turned on to kill unwanted cells or circumscribe wanted cells on the film 312. However, if luminescence were detected during the scout beam traverse, the beam 15 will be attenuated on its return pass. The positive detection of the differentiating signal by the tube 27 ensures the survival of the selected cells. Detection of the edge fluorophore on slides 311a to 311c serves as the boundaries for the scan field of the laser beam 15. The operator need only set the attenuated scout beam 15 on the plate 17. From this point, scanning of the total field is automatic and controlled by the computer 101.

The positive cell selection can be based upon measurements of physical properties such as endogenous fluorescence and de-polarization as well as marker recognition. For more sophisticated applications, actual short experiments can be performed after which selection may be based upon membrane parameters such as rotational and/or translational differences and microviscosity. In all cases, these processes result in the isolation of a viable sub-population of cells or functional clones that have undergone selection without mechanical perturbations.

The instrumentation for these types of measurements can be divided into three (3) groups which are modular in the progression from the simplest to the more complex.

Type I—This apparatus is designed to provide selection based upon the cell's affinity for an internally or externally directed site specific probe that is fluorescently labeled, e.g.-antibodies, lectins, DNA-RNA intercalating dyes. The basic components for this instrument are a tunable argon or argon-krypton laser 10, directing optics 13a to 13e and shutter 21, a microscope 14, a two-dimensional translating stage 16 and photon or rate counter 106a. The instrument is controlled by the computer 101.

Type II—The addition of incident and excitation polarizers and a monochrometer (not shown) in the emission beam before the photomultiplier tube 27 extends the capability of a Type I instrument to select on the basis of the polarization value of various fluorescently depolarizable dyes, e.g.-DPH, and also provide the researcher with the means to select cells that have altered fluorescence emission profiles for cell incorporated or adsorbed dyes. Selection is now based on actual changes in the physical state of the cell rather than purely as a function of the presence or absence of a structural component.

Type III—Since alterations in the membrane dynamics of cells have been demonstrated to be intimately involved in cellular activity, the type III instrument is designed to make its selection on the basis of a real time experiment evaluating lateral and/or rotational diffusion. This type of selection could not be performed on the flow separation system of the prior art due to the necessity for time resolved measurements. Because cells are plated and maintained in a viable environment, long term selections are feasible based on individual cellular experimentation. This type of instrumentation differs from Type II primarily in the computer 101 software and data processing power.

Definable Parameters of Operation

Operator control is attained by keystroke command. In addition to initiating and terminating a sorting process, the following parameters can be scheduled under program control:

(a) two-dimensional stage 16 movement with step magnitude and frequency control.
(b) intensity of analytical (scout) and destroy or fuse beams 11.
(c) threshold beam 11 intensity level.
(d) mode selection—marker or dynamic.
(e) threshold for positive response.
(f) single field scan or continuous mode of operation.

(g) method selection—cell destruction or cell isolation.
(h) beam path radius for cell isolation.
(i) control of all stage 16 operating functions:
  (i) temperature
  (ii) media mixing and flow
  (iii) gas injection
  (iv) growth control additives
  (v) light exposure
  (vi) auxiliary time dependent parameters.

Sorting analysis is now a major research technique in several disciplines, including cancer immunology, hematology, cell cycle analysis, pathology, biochemistry, general immunology and quantitative cytology. New areas of interest for these methods are continuously emerging in cell biology, pharmacology, and toxicology, microbiology and cytogenetics. Diseases now under investigation with cell sorting technology are leukemia, lymphoma, and other cancers, infectious diseases, auto immune diseases, and genetic disorders. The apparatus of the present invention makes reliable cell selection possible for these investigations.

We claim:

1. A method of sorting and separating a heterogeneous population of anchorage dependent living cells comprising:
  (a) providing a film support for the attachment of a heterogeneous population of cells on an underlying surface;
  (b) automatically applying a radiant energy beam at a first intensity to all of said cells on said film support;
  (c) identifying subsets of said cells in said heterogeneous population of cells by response to said beam, with a discriminating means;
  (d) isolating said cells and subsets of said cells of said heterogeneous population of cells by circumscribing desired cells on said film support with a radiant energy beam at a second intensity whereby the film is thermally fused to the underlying surface thereby enabling physical separation by film removal;
  (e) providing selected plural energy levels of said beam to said film support with a control means for selected irradiation, circumscription and isolation of selected cells on said film support surface as indicated by said discriminating means and isolation of selected encountered cells by a circumscribing application of a selected second energy intensity of said beam.

2. An apparatus for automatically sorting and separating selected types of cells from a heterogeneous population of anchorage dependent living cells comprising:
  (a) an underlying surface;
  (b) a film support over said underlying surface and said film support sustaining an attached heterogeneous population of cells;
  (c) a focussed radiant energy beam at a first intensity traversing all of said cells on said film, said focused radiant energy beam and said underlying surface movable in respect to each other;
  (d) discriminating means identifying said cells and subsets of said cells in said heterogeneous population of cells on said film in response to said first intensity;
  (e) a focussed radiant energy beam at a second intensity level isolating selected of said subsets of said cells by circumscribing desired cells on said film support and thermally fusing said film to said underlying surface thereby enabling physical separation by removal of said circumscribed film support;
  (f) coordinating means selecting said plural energy levels of said beams and movement of said beams for selected irradiation, discrimination, and circumscription prior to the isolation of said selected cells on said film support surface.

3. The apparatus of claim 2 wherein said support is a plate covered by a film on said plate beneath said cells and said film is bondable by said beam to said plate at selected energy intensity of said beam and isolating cells within a circumscribed area; and said film thus circumscribed removable from the said plate to achieve removal and destruction of unwanted cells from said plate.

4. An apparatus in accord with claim 2 in which selected drive means is coordinated with said support means for selected automatic and manual coordination with said detecting means and said radiant energy beam to sort out and save selected cells and destroy selected other of said cells and the organic residue from said destruction being isolated from said saved cells.

5. The apparatus of claim 2 wherein the discrimination means to identify wanted cells from unwanted cells on the support comprises a photomultiplier tube responding to selected physical, chemical and dynamic properties of some of said cells and not others to identify selected cells by responding to cell reaction to said beam attenuated to signal the selection.

6. The apparatus of claim 2 wherein a memory records said location of said cells and controls selected return to said location at a selected circumscribing and isolating energy intensity for circumscription of selected of said cells and for isolation therefrom of other and unselected of said cells.

7. The apparatus of claim 2 wherein the identification means is a photomultiplier tube which coordinates with the position of said cells on said support surface at selected luminescence in a first irradiation at a first energy intensity trace of said beam and thereupon returning to said selected cells at higher beam intensity excising certain of said selected cells and leaving circumscribed cells segregated in situ.

8. The apparatus of claim 2 wherein programmed computer means are provided responsive to sensing by a photomultiplier tube during scan of said cells in situ on said film on said support surface at selected energy intensities, said computer means controlling said beam and its selected attenuation firstly to irradiate said cells in a prearranged path on said film support surface and then in selected isolation and removal of one group of said cells as selected in situ on said film.

* * * * *